United States Patent [19]

Firestone

[11] Patent Number: 4,719,312

[45] Date of Patent: Jan. 12, 1988

[54] LYSOSOMETROPIC DETERGENT THERAPEUTIC AGENTS

[75] Inventor: Raymond A. Firestone, Fanwood, N.J.

[73] Assignee: Merck & Co., Inc., Rahway, N.J.

[21] Appl. No.: 902,136

[22] Filed: Sep. 2, 1986

Related U.S. Application Data

[63] Continuation of Ser. No. 536,139, Sep. 26, 1983, abandoned, which is a continuation of Ser. No. 297,443, Aug. 28, 1981, abandoned, which is a continuation-in-part of Ser. No. 250,372, Apr. 2, 1981, abandoned, which is a continuation-in-part of Ser. No. 209,815, Nov. 24, 1980, abandoned, which is a continuation-in-part of Ser. No. 176,238, Aug. 8, 1980, abandoned, which is a continuation-in-part of Ser. No. 947,374, Oct. 2, 1978, abandoned.

[51] Int. Cl.$^4$ .............................................. C07C 87/22
[52] U.S. Cl. ...................................................... 564/510
[58] Field of Search ........................................ 564/510

[56] References Cited

U.S. PATENT DOCUMENTS

| | | | |
|---|---|---|---|
| 3,077,499 | 2/1963 | Tullock | 564/510 |
| 3,118,945 | 1/1964 | Cohen | 564/510 |
| 3,214,412 | 10/1965 | Brown | 564/510 |
| 4,059,629 | 11/1977 | Foulletier et al. | 564/510 |

OTHER PUBLICATIONS

"Lysosomotropic Agents. 1. Synthesis and Cytotoxic Action of Lysosomotropic Detergents", *Journal of Medicinal Chemistry*, vol. 22, No. 9, 1979, pp. 1130-1133.

*Primary Examiner*—Glennon H. Hollrah
*Assistant Examiner*—John A. Sopp
*Attorney, Agent, or Firm*—Charles M. Caruso; Hesna J. Pfeiffer

[57] ABSTRACT

The present invention is concerned with the preparation of lysosomotropic detergent agents and pharmaceutical composition useful in the treatment of cancer. These compounds are amine derivatives having a pK of 3.5 of the general structure

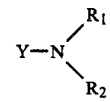

in which $R_1$ is $C_{8-30}$ alkyl, $C_{8-30}$-alkenyl, substituted $C_{4-30}$ alkyl or substituted $C_{4-30}$-alkenyl; $R_2$ is hydrogen or $C_{1-4}$ alkyl and Y is an electron withdrawing group, to control the pK, selected from trifluoroethyl, and difluoroethyl.

3 Claims, No Drawings

LYSOSOMETROPIC DETERGENT THERAPEUTIC AGENTS

CROSS-REFERENCE TO RELATED APPLICATIONS

This is a continuation of application Ser. No. 536,139, filed Sept. 26, 1983, now abandoned, which is a continuation of application Ser. No. 297,443, filed Aug. 28, 1981, now abandoned, which in turn is a continuation-in-part of application Ser. No. 250,372, filed Apr. 2, 1981, now abandoned, which in turn is a continuation-in-part of application Ser. No. 209,815, filed Nov. 24, 1980, now abandoned, which in turn is a continuation-in-part of application Ser. No. 176,238, filed Aug. 8, 1980, now abandoned, which in turn is a continuation-in-part of application Ser. No. 947,374, filed Oct. 2, 1978, now abandoned.

BACKGROUND OF THE INVENTION

1. Field of the Invention

The present invention relates to compositions useful in the control of fertility, and also to composition useful in the inhibition of malignant cell growth and in the control of diseases which accumulate cells such as macrophages, polymorphonuclear leukocytes, platelets, etc., at the disease site. More specifically, it relates to novel chemical compositions and pharmaceutical formulations comprising a weakly basis amine or a nitrogen-containing heterocyclic compound having a pK of from 3.5 to 8, incorporating a hydrophobic moiety.

The present invention also relates to novel weakly basic amine compounds.

Lysosomotropic substances are substances which are selectively taken up by lysosomes, which are present in most animal cells. The property of lysosomotropism is thus useful in the preparation of therapeutic agents since these agents can enter the lyosomes preferentially and exert their biological influence by disrupting the lysosomes. They also can be coupled with active drugs and, following preferential uptake by lysosomes, can be hydrolyzed within the lysosome with release of the active drug at the target area.

Lysosomes are membrane-bound organelles containing a variety of hydrolytic enzymes that would be cytotoxic if released within the cell. Lysosomes function to destroy invading microorganisms, which is accomplished by phagocytosis; to disposed of exhausted cell components; and to break down nutrient materials within the cell, which is accomplished by endocytosis. When the nutrient material is dissolved in water, the process is called pinocytosis. A common aspect of all three processes is that the cell's outer membrane engulfs the microorganism, particle, or liquid droplet, forming a membrane-bound vesicle that is internalized and is then fused with a lysosome for chemical treatment. Normally, at all times the lysosomal contents are separated from the cytosol by a membrane.

A significant feature of the interior environment of the lysosome is its acidity. The intralysosomal pH is between 3 and 5, compared to a normal cell interior envionment pH of about 7, i.e., neutral. The importance of this feature will be described further below.

If the lysosome membrane is ruptured, the lysosome then pours out into the remainder of the cell in which it is contained, its contents of powerful hydrolytic enzymes, which soon results in destruction of the cell itself. This action can be used to therapeutic advantage in a number of ways, as will be detailed below.

The lysosomal membrane is a bilayer membrane sheet, e.g., like that formed by phospholipids such as lecithin. The molecular units from which the bilayer membrane is formed are composed of a lipophilic portion at one end, comprising two parallel elongated segments, and at the opposite end, a hydrophilic portion. The molecular structure of these units enables them to form stable bilayers of indefinitely large extension. This is in contrast to the molecular structure of detergents which, while they have opposing lipophilic and hydrophilic portions, are characterized by a lipophilic portion comprising only one elongated segment. Detergents cannot form large stable bilayers, but only small ones called micelles which have small radii of curvature. Consequently, when a detergent is introduced into the bilayer membrane of a lysosome, which is readily accomplished because of the similarity in structure, the detergent units disrupt the lysosome membrane and ultimately result in its rupture.

However, it is not practical to rupture the lysosomal membrane by using ordinary detergents, since they are indiscriminate as to membrane type and will attack the cell membrane first. This basic impediment was overcome in designing the compounds of the present invention by taking advantage of the difference between the intralysosomal pH and pH of the cell interior environment, i.e., of the cytosol or intercellular fluid. This difference amounts to from 2 to 4 pH units.

More specifically, the weekly basis amines or nitrogen-containing heterocyclic compounds of the present invention have a pK value of from 3.5 to 8, hereby they become substantially protonated inside, but not outside of the lysosomes, due to the pH difference between the lysosome and the remainder of the cell. Protonation gives the compound the hydrophilic portion of its molecular structure, and since it already possesses a lipophilic portion, it becomes, at that point, a lysosomotropic detergent. The protonated species, which is ionized, is thermodynamically more stable within the lysosome than in the cytosol, and so will accumulate there, until its concentration is as much as 1000 times that in the cytosol. Also, the ionization of the compound inhibits its passing out through the lysosomal membrane.

The lysosomotropic detergent accumulates in the bilayer of the lysosomal membrane, which gradually weakens, breaking up when some point related to the critical micelle concentration of the protonated species is reached.

The weakly basic amine and nitrogen-containing heterocyclic compound lysosomotropic detergents of the present invention have utility in several therapeutic areas as a result of their ability to rupture the lysosomal membrane, as described above.

For example, the compositions of the present invention have anti-fertility, i.e., contraceptive activity through their ability to interfere with the functioning of the specialized lysosome of the sperm cell, which is called the acrosome.

2. Brief Description of the Prior Art

The concept of lysosomotropic drugs was originated by (1) De Duve et al., *Biochem. Pharmacol.*, 23, 2495 (1974), and has been applied to the treatment of leukemia using DNA complexes of adriamycin and daunorubucin; (2) Trouet et al., *Nature* (London), *New Biol.*, 29, 110 (1972); and (3) Trouet et al., *Eur. J. Cancer*, 10, 405 (1974).

Compounds useful in the compositions and methods of the present invention are described in a number of publications, none of which, however, describe or suggest the particular use in which these compounds have been put in the present invention. Reference is made, for example, to the following such publications: (4) Wibaut et al., *Rec. Trav. Chim.*, 72, 513 (1953); (5) Shelton et al., U.S. Pat. No. 2,446,792; (6) Techitchibabine, *Bull. Soc. Chim.*, 5, 429 (1938); (7) Wibaut, *Rec. Trav. Chim.*, 63, 141 (1944); (8) King et al., *J. Econ. Entomol.*, 37, 629 (1944); (9) Birchenough, *J. Chem. Soc.*, 1951, 1263; (10) Knight et al., *J. Chem. Soc.*, 1938, 682; (11) Niederl et al., U.S. Pat. No. 2,602,791; (12) Niederl et al., *JACS*, 70, 618; (13) Gitterman et al., U.S. Pat. No. 3,718,651; and (14) Shen et al., U.S. Pat. No. 3,840,542;

Compounds related to the novel weakly basic amine compounds of the present invention are described in (15) Foulletier et al. U.S. Pat. No. 4,059,629; (16) Brown U.S. Pat. No. 3,214,412; and (17) Husted U.S. Pat. No. 2,727,923. However, none of these patents describe or suggest the particular amines of the present invention, which must be 2,2-difluoro- or 2,2,2-trifluoroethyl, and thus have a methylene bridge between the flourinated methyl electron-withdrawing group and the nitrogen atom.

Husted, for example, teaches a methylene bridge, but only in association with a fluorinated alkyl group of at least 3 carbon atoms. For each amines to be useful in the compositions of the present invention, they must have an ethylene bridge separating the fluorinated alkyl group from the nitrogen atom. Further, Husted does not disclose the lipophilic alkyl substituent of 8 to 30 carbon atoms.

Brown teaches only difluoromethylamines.

Foulletier discloses compounds useful in the compositions of the present invention, but does not teach the novel amine compounds of the present invention. Thus, Foulletier discloses only 3,3,3-trifluoropropylamine, rather than 2,2difluoro- or 2,2,2-trifluoroethylamine.

As will be shown in more detail below, the related amine compounds of the prior art do not possess properties sufficient for use in the compositions and methods of the present invention.

SUMMARY OF THE INVENTION

The present invention is concerned with the inhibition and destruction of lysosome-bearing cells.

More particularly, the present invention is concerned with novel compounds, pharmaceutical compositions, and methods of treatment which are useful in inhibiting the function of lysosome-bearing cells.

The present invention comprises novel spermicidal pharmaceutical compositions useful in reducing fertility comprising a pharmaceutical carrier and a therapeutically effective amount of a lysosomotropic substance comprising (a) a weakly basic amine having a pK of from 3.5 to 8 and (1) at least one lipophilic substituent comprising an alkyl or aklenyl substituent having at least 8 carbon atoms, a substituted alkyl or alkenyl substituent, or a perfluorinated alkyl group of from 3 to 20 carbon atoms, and (2) an electron-withdrawing group; or (b) a nitrogen-containing heterocyclic compound having a pK of 3.5 to 8 and a lipophiic substituent comprising any one of the radicals employed for that purpose in the weakly basis amines described above, or additionally 3-cholesteryl.

More specifically, the present invention comprises novel spermicidal pharmaceutical compositions useful in reducing fertility comprising a pharmaceutical carrier and a therapeutically effective amount of (a) an amine compound having a pK of from 3.5 to 8 of the formula:

wherein:

$R_1$ is $C_{8-30}$ alkyl or $C_{8-30}$ alkenyl, or substituted $C_{4-30}$ alkyl or substituted $C_{4-30}$ alkenyl;

$R_2$ is hydrogen or $C_{1-4}$ alkyl; and

Y is an electron-withdrawing group to control the pK of the amine between 3.5 and 8 comprising trifluoroethyl, difluoroethyl, carboxymethyl, cyanoethyl, hydroxy, methoxy, amino, alkylamino, or acylamidino; or a nitrogen-containing heterocyclic compound having a pK of from 3.5 to 8 of the formula:

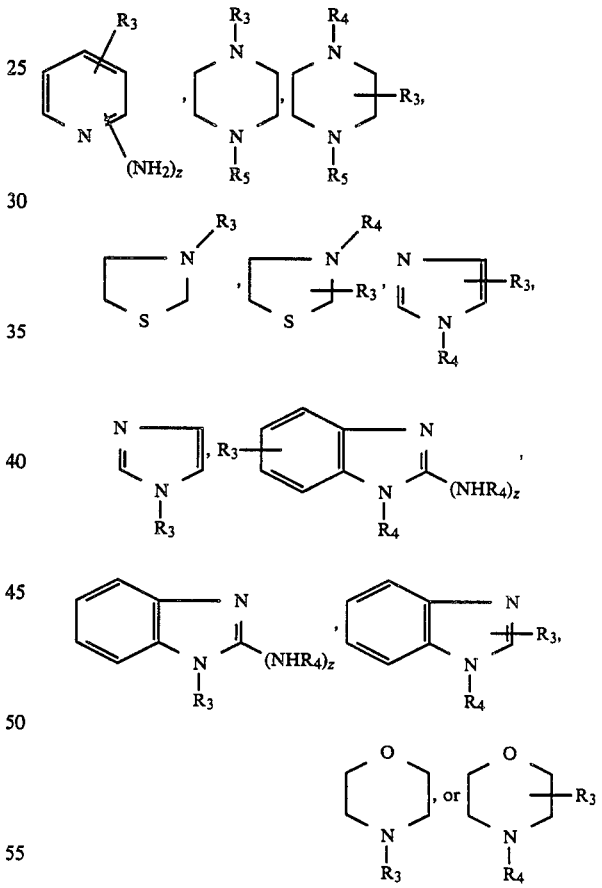

wherein:

z is either 0 or 1;

$R_3$ is $C_{8-30}$ alkyl or $C_{8-30}$ alkenyl, or substituted $C_{4-30}$ alkyl or substituted $C_{4-30}$ alkenyl; 3-cholesteryl; or retinyl;

$R_4$ is selected from H or loweralkyl; and $R_5$ is acyl comprising —COOR or —COR in which R is $C_{1-4}$ alkyl aryl comprising phenyl, tolyl, xylyl, or naphthyl; arylsulfonyl in which aryl has the same meaning as above;

or phosphoryl (=PO).

The lipophilic and electron-withdrawing functionalities of the amine compounds in (a) above may be combined in a single perfluoroalkyl substituent of the formula: $C_nF_{2n+1}$, where n is from 3 to 20. Such a perfluoroalkyl group is joined to the nitrogen atom of the amine group by an alkylene bridge of 1 to 3 carbon atoms. Thus, the formula for the amine group becomes:

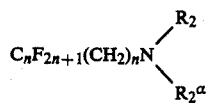
(II.)

where $R_2^\alpha$ has the same meaning as $R_2$, which is defined as above, and n is 1 to 3.

Preferred novel spermicidal pharmaceutical compositions of the present invention are those containing the following active ingredients, which are arranged in order of increasing potency:

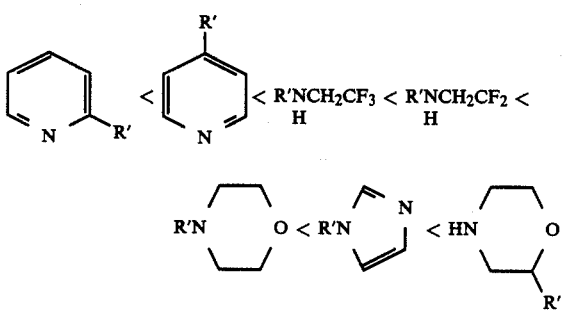

where R'=dodecyl.

As antifertility agents, the active ingredient, for example, N-dodecyl imidazole, is incorporated into vaginal cream, jellies, or foams in a concentration of from 0.1% to 10%, preferably 1-5%. The formulation prepared in this manner is administered intravaginally and contact of the sperm with the composition of the present invention incorporates the active principle into the acrosome of the sperm cells, thereby rendering them infertile.

The active ingredients of the novel compositions of the present invention described above may enter a target cell in different ways. Provided that its molecular weight is sufficiently low, the active ingredient may enter the cell by passive diffusion, whereby it merely passes through the cell membrane without hindrance. The active ingredient may also enter the cell by endocytosis, or more particularly, by pinocytosis. In this mode of entry, the outer cell membrane invaginates about a drop of liquid in which the active ingredient is dissolved, thereby incorporating it within the cell proper. This drop then approaches and fuses with a lysosome within the cell, forming a secondary lysosome in which digestion takes place.

Passive diffusion as a mode of entry is nonspecific, i.e., the lysosomotropic detergents of the present invention can enter many different cells by this mode, and cytotoxicity will ultimately result where the cells contain lysosomes. In order to afford specificity, by leaving pinocytosis as the only viable mode of entry, certain novel peptide conjugates of the present invention have been prepared. These peptides are designed to be susceptible to intralysosomal hydrolysis to the active detergents by lysosomal enzymes known to be present in most cell types.

The specificity of the novel peptide conjugates can be an important advantage in treating cells which are more pinocytic than other cells.

Another aspect of the selectivity of the novel peptide conjugates of the present invention is that only cells with lysosomes are affected since intralysosomal hydrolysis is required for activation. Thus, the stem cells of human bone marrow, essential to formation of leukocytes, would remain unaffected.

Another advantage of the novel peptide conjugates of the present invention is that they may act more quickly than the lysosomal detergents from which they are derived.

This faster action by the novel peptide conjugates of the present invention is due, it is believed, to facilitated pinocytosis, wherein pinocytosing cells are characterized by one or more active transport systems which accelerate pinocytosis for certain chemical entities which the cell recognizes. The novel peptide conjugates of the present invention possess the necessary chemical identity to take advantage of the active transport systems of the pinocytosing cells, and yet at the same time are susceptible to intralysosomal hydrolysis.

The novel peptide conjugates of the present invention, useful as active ingredients in spermicidal pharmaceutical compositions for reducing fertility, have the general formula:

(III.)

wherein
A is a peptide moiety that is capable of being hydrolyzed intralysosomally selected from the group consisting of Gly-Phe, Arg-Arg, benzoyl-Arg, Val-Leu-Lys, and Ala-Arg-Arg;
B is a conventional peptide blocking group, for example CBZ or BOC, or is not present; and
Y and $R_1$ are as defined above.

In accordance with accepted practice, CBZ designates the benzyloxycarbonyl protecting group and BOC designates the t-butyloxycarbonyl protecting group.

As described above, the novel compositions of the present invention are effective spermaticidal agents useful in reducing fertility. However, the novel compositions of the present invention also find usefulness in other areas of therapeutic treatment. For example, the active ingredients of Formulas I, II and III are effective carcinostatic agents which can be used successfully to kill cancer cells. This action is achieved through the same mechanism of lysosomotropism, detergent rupture of the lysosomal membrane, and resulting cytotoxicity, as characterized the action of the spermaticidal agents.

A particular carcinostatic agent of Formula I of the present invention is the novel compound, N-retinyl morpholine, which may be represented by the following formula:

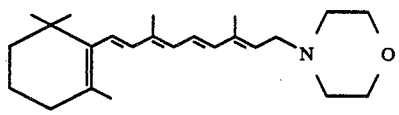

It is known that vitamin A derivatives have anti-cancer activity, and preparation of new retinoids for this and related purposes is an active field. See Y. Fujimaki, *J. Cancer Res.*, 10, p. 469 (1926) and H. Mayer et al., *Experientia*, 34, p. 1105 (1978). There is also evidence that one site of action may be the lysosomal membrane. See Dingle and Lucy, *Biol. Rev.*, 40 p. 422 (1965); W. Bollag, *Cancer Chemo. Rep.*, 55, p. 53 (1971); R. J. Shamberger, *J. Nat. Can. Inst.*, 41, p. 667 (1971); and Bard and Lasnitzki, *Brit. J. Cancer*, 35, p. 115 (1977). However, none of the above suggest the use of the novel N-retinyl morpholine of the present invention as an anti-cancer agent.

The novel peptide conjugates of Formula III have led to the development of novel peptide conjugates of the formula:

B-A-N-Q     (IV)

wherein:
A and B are the same as above, and
N-Q represents a therapeutic entity (Q) bound to the peptide portion (A) of the compound through the nitrogen atom (N).

The novel peptide conjugates of Formula IV may be used to treat inflammation, and diseases where the disease causing microorganism resides in cell lysosomes, as will be described in more detail below.

The novel peptide conjugates of Formula IV are also especially suitable carcinostatic agents, since they have improved selectivity due to the fact that (1) pinocytosis is the primary or exclusive mode of entry into the cell for these compounds, and malignant cells are often more pinocytic than normal cells; and (2) cells without lysosomes, such as bone marrow stem cells, are not affected. This is an improvement over prior art methods which have sought to use exogenous toxic agents as a complex which could be decomplexed within the lysosome, thereby killing the cell involved. Such decomplexation might not always be limited to the intralysosomal environment.

An example of a carcinostatic agent of Formula IV is one employing the potent anti-cancer agents described in U.S. Pat. Nos. 3,718,651 and 3,840,542, for example the following compound:

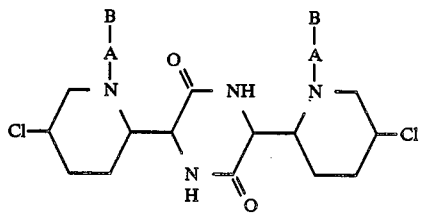

This compound would thus comprise the N-Q portion of Formula IV.

The above compound is related to nitrogen mustard, which has the following formula:

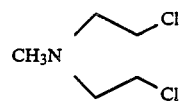

Nitrogen mustard may also be used as the N-Q portion of Formula IV, for example as in the following compound:

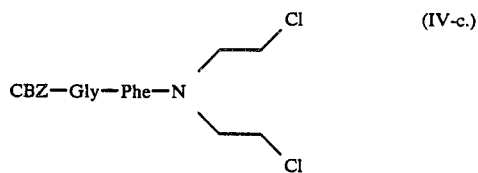

In the above formula the carbonyl group, which is not shown specifically, is part of the Phe group. The amide linkage which is thus formed deactivates the nitrogen atom since there is no longer an unshared pair of electrons on the nitrogen atom. In this way the carcinostatic agent is made even more selective since it will have no activity until the compound of Formula IV is hydrolyzed within cell lysosomes, releasing the carcinostatic agent.

A further example of a carcinostatic agent of formula IV is one in which the cytotoxic agents doxorubicin (also known as adriamycin or 14-hydroxydaunomycin or daunorubicin (also known as daunomycin) comprise the N-Q portion of formula IV. The structural formulas of these compounds which can comprise the N-Q portion of formula IV follow:

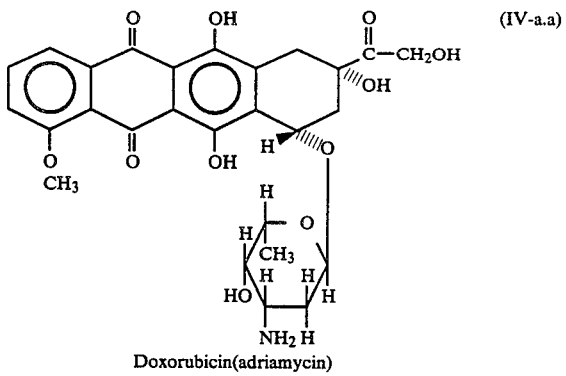
Doxorubicin(adriamycin)

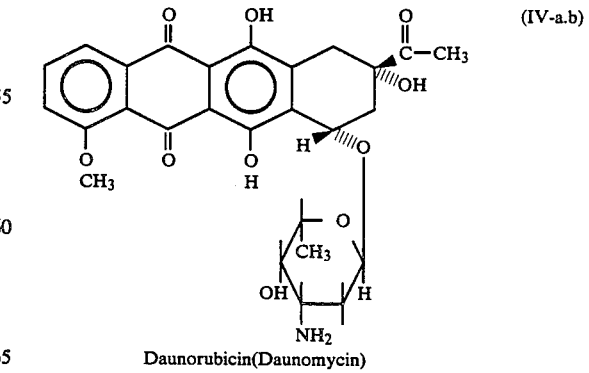
Daunorubicin(Daunomycin)

These compounds are linked through the amino sugar moiety as illustrated below in the case of doxorubicin.

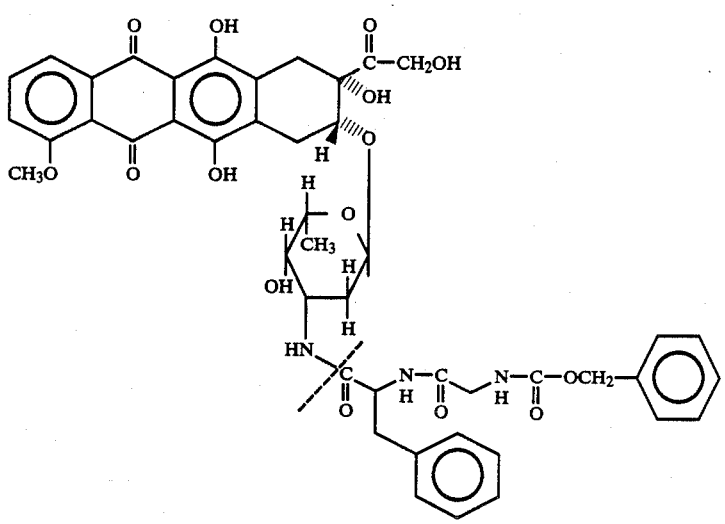
(IV-a.a.1)

The dotted line in the formula indicates the anticipated hydrolytic scissium locus.

A still further example of a carcinostatic agent of formula IV is one in which the cytotoxic agent 5-fluorouracil is employed as the N-Q portion of Formula. The compounds employing 5-fluorouricil are shown in the following formulas:

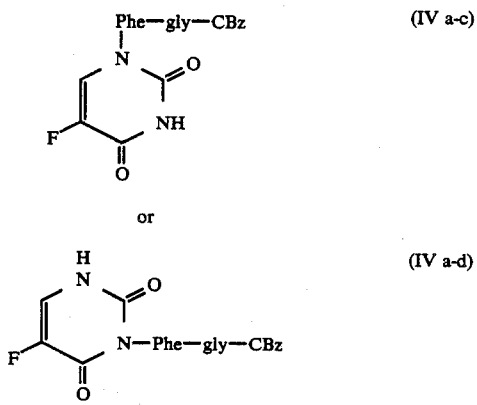

As described above, the novel peptide conjugates of Formula IV may also be utilized to deliver an antiinflammatory agent to a site of inflammation. Thus, a composition of an antiinflammatory steroid or nonsteroid coupled to a lysosomally cleavable peptide through an amine function of the steroid or non-steroid is cleaved by lysosomal enzymes at the site of inflammation, thereby producing the desired antiinflammatory effect with reduced side effects. The following is an example of two such compounds:

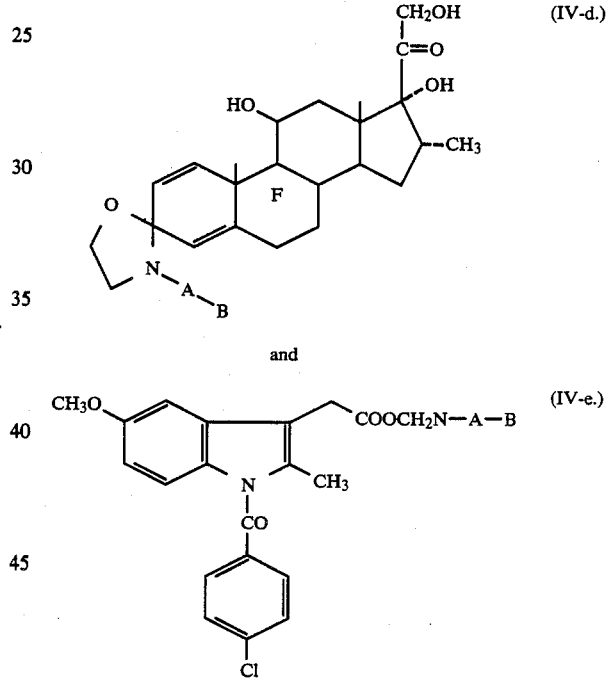

Inflammation sites are characterized by a large number of macrophages, which contain many lyososomes. As a result, a certain specificity of transport is achieved, since the anti-inflammatory drug will be released systemically to a much lesser extent. This low systemic release level, in turn, accounts for the reduced incidence of side effects, which are symmetrically derived.

Further, as described above, the novel peptide conjugates of Formula IV are useful in treating diseases where the microorganism causing the disease resides within the lysosomes of various body cells, and is thus to some extent unreachable by commonly used antimicrobial and other therapeutic agents. Diseases of this type include leprosy, tuberculosis, and clinically resistant bacterial infections which cannot be successfully treated with cephalosporin and aminoglycoside agents.

For example, cephalosporin agents are active only as the free acid, and due to the low pH within lysosomes, tend to concentrate in the cytosol as the more stable carboxylate ion form. The novel peptide conjugate of the present invention overcomes this problem by forming a lysosomotropic combination which will release the cephalosporin agent within the lysosome. These particular peptide conjugates may be represented by the formula:

$$\text{(IV-f.)}$$

[Structure with $R_5$, $R_6$, $R_7$, S, N, $CH_2R_8$, $COOCH_2N-A-B$]

wherein
$R_5$ is phenyl; substituted phenyl; 2- or 3-thienyl; 2- or 3-furyl;
$R_6$ is amino or hydrogen;
$R_7$ is hydrogen or methoxy; and
$R_8$ is hydrogen; pyridinium; carbamate; or $$\begin{array}{c} CH_3 \\ N-N \\ -S \\ N-N \end{array}$$

Other anti-microbial agents which may be utilized in a similar manner to form the novel peptide conjugates of the present invention are the various penicillins, which may be represented by the formula:

$$\text{(V.)}$$

[Structure with $R_5$, $R_6$, S, $CH_3$, $CH_3$, N, $COOCH_2N-A-B$]

where $R_5$ and $R_6$ have the same meaning as above.

Another particularly useful anti-microbial agent which may be utilized to form the novel peptide conjugates of the present invention is thienamycin, which may be represented by the formula:

$$\text{(VI)}$$

[Structure with OH, S, $R_9$, N, $COOCH_2N-A-B$]

where $R_9$ is $-NH_2$ or $$-\overset{H}{N}-CH_2=\overset{+}{N}H_2-Cl$$

The compounds of this invention can be administered either topically or systemically, i.e., intravenously, subcutaneously, intramuscularly, orally, rectally, by aerosolization, or in the form of sterile implants for long action.

The pharmaceutical compositions can be sterile, injectable suspensions or solutions, or solid, orally administrable, pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" refers to physically discrete units suitable as unitary dosages for animal and human subjects, each unit containing a predetermined quantity of active material calculated to produce the desired biological effect in association with required pharmaceutical means.

The low cost and ready accessibility of the compositions of this invention make them particularly promising for applications in veterinary medicine in which field their utilities are comparable to those in human medicine.

The amount of active ingredient that may be combined with the carrier materials to produce a single dosage form will vary depending upon the host treated and the particular mode of administration. For example, a formulation intended for the oral administration of humans may contain from 1 mg. to 50 mg. of active agent compounded with an appropriate and convenient amount of carrier material which may vary from about 5 to about 95 percent of the total composition. Dosage unit forms will generally contain between from about 0.1 mg. to about 100 mg. of active ingredient.

Compounds of Formula I are readily prepared by reaction of an amine of the formula:

$$\begin{array}{c} R_1 \\ \phantom{R_1}\diagdown \\ \phantom{R_1R_1}NH \\ \phantom{R_1}\diagup \\ R_2 \end{array}$$

with an anhydride or an ester of a fluorinated lower aliphatic carboxylic acid to produce an amide compound of the formula:

$$\begin{array}{c} R_1 \phantom{xxxx} H_x \\ \phantom{R_1}\diagdown \phantom{xx} | \\ \phantom{R_1R_1}N-CO(CH_2)_nC-F_y \\ \phantom{R_1}\diagup \\ R_2 \end{array}$$

wherein n is an integer of from 1–8 inclusive, x is 0 or 1, and y is 2 or 3 provided that the sum of x and y is 3.

The resulting amide compound is then reduced to the desired amine product by treatment with a reducing agent such as borane in a suitable aprotic solvent such as tetrahydrofuran at a temperature of from 0° C. to the reflux temperature of the reaction mixture for a period of from 1–24 hours.

The preparation of the compounds of Formula I described above may be schematically illustrated as follows:

$$RNH_2 + TFAA \longrightarrow RNHCOCF_3 \xrightarrow{BH_3} RN\overset{H}{}CH_2CF_3$$

$$RNH_2 + CHF_2COOEt \longrightarrow$$

$$RNHCOCHF_2 \xrightarrow{BH_3} RN\overset{H}{}CH_2CHF_2$$

Examples of such amines are N-fluoroalkylamines such as
N-dodecyl-2,2,2-trifluoroethylamine;
N-octyl-2,2,2-trifluoroethylamine;
N-decyl-2,2,2-trifluoroethylamine;
N-hexadecyl-2,2,2-trifluoroethylamine;
N-octadecyl-2,2,2-trifluoroethylamine;

N-dodecyl-2,2-difluoroethylamine.

The nitrogen-containing heterocyclic compounds used in the pharmaceutical compositions of the present invention may be prepared, for example, in accordance with the procedures schematically represented as follows:

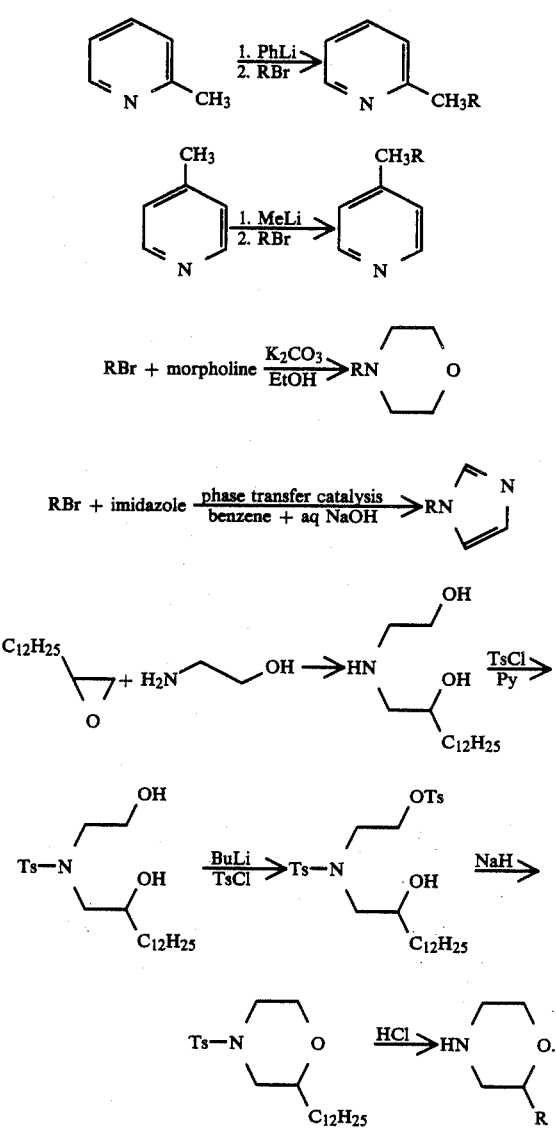

Examples of such heterocycles are N-alkyl pyridines such as N-nonyl, N-tridecyl, N-heptadecyl, and N-nonadecyl pyridine; 2-alkyl pyridines such as 2-nonyl, 2-tridecyl, 2-heptadecyl, and 2-nonadecyl pyridines; N-alkyl morpholines such as N-decyl, N-dodecyl, N-tetradecyl, N-hexadecyl, and N-octadecyl morpholines; and alkyl-substituted imidazoles such as N-dodecylimidazole.

The novel compound N-retinyl morpholine may be prepared by converting retinol to the tosylate through activating with very strong base, and then treating the tosylate, without purification with morpholine. The reaction sequence may be illustrated as follows:

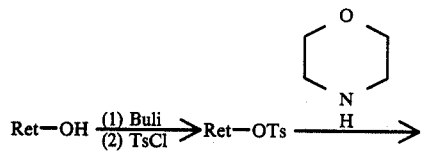

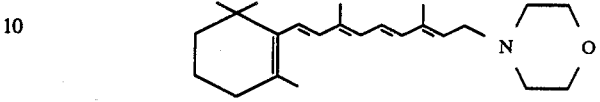

Compounds of Formula III are readily prepared by reaction of the selected amine with a selected peptide in the presence of a substance such as dicyclocarbodimide under anhydrous conditions.

The following examples further illustrate preparation of various compounds and pharmaceutical compositions of the present invention.

EXAMPLE 1

N-Dodecyl difluoroacetamide

One equivalent difluoroethylacetate and one equivalent dodecylamine stirred at room temperature in acetonitrile 16 hours. The solvent is removed to give a white wax, which is chromatographed on silica gel in CHCl₃/EtOAc (15:1), $R_f$=0.7. NMR (CDCl₃, δ) 7.2 b-s (1H); 5.9 g (2H) J=26; 3.35 m (2H); 1.3 s (20H); 0.9 m (3H). Other compounds prepared this way, with similar NMR, acceptable Mass Spectra and TLC: N-propyl-difluoroacetamide.

EXAMPLE 2

N-Dodecyl-trifluoroacetamide

Trifluoroacetic anhydride (21 ml; 1.5 equivalents) is added dropwise to a stirring solution of 17.9 g. dedecylamine (1 equivalent) and 13.5 ml. triethylamine (1 equivalent) in 100 ml. CH₂Cl₂ at 0° C. over 30 minutes, and the mixture stirred at room temperature 30 minutes. It is washed with water, 1M H₃PO₄, brine, dried over MgSO₄, filtered, stripped to yield 26.01 g. product (96%). TLC in cyclohexane/EtAc (10:1) gives one spot at $R_f$—0.5 and no starting material ($R_f$—0.05). NMR (δ, CDCl₃): 6.19 bs (1H); 3.30 q, J=4 (2H); 1.20 s (20H); 0.92 m (3H).

The following similar compounds were all prepared in the same manner, all with similar NMR, acceptable microanalyses, mass spectra, and single spot on TLC: N-propyl-trifluoroacetamide, N-pentyl-trifluoroacetamide, N-octyl-trifluoroacetamide, N-decyl-trifluoroacetamide, N-hexadecyl-trifluoroacetamide, N-octadecyl-trifluoroacetamide.

EXAMPLE 3

N-Dodecyl-2,2,2-trifluoroethylamine

A solution of 8 ml. BH₃ in THF (8 mM) is added dropwise to a solution of 1.12 g. (4 mM) dodecyl-trifluoroacetamide in 6 ml. THF at 0° C. under N₂. The mixture is refluxed 16 hours, cooled in ice, and 6 ml. concentrated HCl added slowly. The THF is distilled off at atmosphere pressure, the mixture cooled in ice, and solid NaOH added slowly with cooling until alkaline to pH paper. The aqueous solution is then extracted three times with hexane. The combined organic layers are washed with water, dried over K₂CO₃, filtered, stripped to give 2.0 g. crude product. It is then chromatographed in cyclohexane/EtOAc (10:1) on silica gel ($R_f$=0.4) to give 870 mg. oil which is distilled at 0.3 mM., b.p. 135° C., to give 405 mg. pure product, 38% yield. NMR (CDCl$_3$, δ): 3.22 q, J=10 (2H); 2.79 m (2H); 1.40 s (20H); 0.93 m (3H). IR shows no carbonyl bands.

Other compounds made this way, all with similar NMR and other spectral data:
N-octyl-2,2,2-trifluoroethylamine;
N-decyl-2,2,2-trifluoroethylamine;
N-hexadecyl-2,2,2-trifluoroethylamine;
N-octadecyl-2,2,2-trifluoroethylamine;
N-dodecyl-2,2-difluoroethylamine.

EXAMPLE 4

N-Carbobenzoxy-glycyl-N-dodecyl phenylalanineamide

Dodecylamine (924 mg.) in 20 ml. THF is added dropwise to a 0° C. solution of 1.78 g. z-Gly-Phe and 1.02 g. DDC in 30 ml. THF under N$_2$ and stirred at 0° C. for 4 hours. The reaction mixture is filtered, the filtrate evaporated in vacuo to give 3.53 g. crude product, which was chromatographed on 100 g. silica gel in CHCl$_3$/EtOAc (2:1) to give 890 mg. product (34%). NMR (CDCl$_3$, δ): 7.7m (1H); 7.3 d (10 Hz); 6.6 m (1H); 6.2 (1H); 5.2 s (2H); 4.8 m (1H); 3.9 d, J=6 Hz (2H); 3.1 m (4H); 1.3 bs (20H); 0.9 m (3H).

Other compounds made this way with similar spectral data:
N-carbobenzoxy-glycyl-N-dodecyl-N-2,2,2-trifluoroethyl-phenylalanineamide.

EXAMPLE 5

N-Dodecyl Imidazole

A stirred mixture of 9.96 g. of dodecyl bromide (40 mM), 5.44 g. of imidazole (80 mM), 100 ml. of 0.97N NaOH (97 mM), 100 ml. of PhH, and 336 mg. of Aliquat 336 (1 mM; methyltricaprylylammonium chloride) was refluxed for 23 h. The benzene layer was separated, washed with brine containing a little NaOH, and evaporated. The residue was purified of a little front-running and some origin impurities by quick chromatography on 150 g. of silica gel with 1:1 CH$_2$Cl$_2$—EtOAc ($R_f$ 0.35), affording 7.48 g. of single-spot material which was distilled at ca. 0.5 Torr (bp 144° C.) to give 6.97 g. of pure product (74%): NMR 7.5 (s, 1H), 7.1 (br s, 1H), 6.95 (br s, 1H), 3.95 (t, J=7 Hz, 2H), 1.85 (m, 2H), 1.3 (s, 18H), 1.0 ppm (m, 3H).

EXAMPLE 6

N-Retinyl Morpholine

To a solution of 1.258 g. (4.4 mM all-trans retinol in 10 ml. of tetrahydrofuran at −78° C. under nitrogen was added 2 ml. (4.4 mM) of 2.2M of n-butyllithium. After stirring 5 min., 836 mg. (4.4 mM) tosyl chloride was added, and the reaction mixture was stirred 1 hr. at −78° C. Then 2 ml. of morpholine were added, and the reaction mixture was allowed to warm to room temperature. After removal of solvent under vacuum, the residue was taken up in n-hexane, filtered and evaporated under vacuum, leaving 1.5 g. crude product. This was dissolved in ether, and 2 g. of p-toluenesulfonic acid in 15 ml. of ether was added dropwise. The resulting precipitate was filtered, and shown to be N-retinyl morpholine. TsOH by NMR. The free base was liberated with saturated aqueous sodium bicarbonate, extracted with ether, dried over potassium carbonate, filtered and evaporated under vacuum, giving 594 mg. of pure N-retinyl morpholine.

EXAMPLE 7

Contraceptive Formulations

A suitable formulation is prepared by mixing the lysosomotropic amine and other ingredients employed in the following proportions (in percentages):

| | |
|---|---|
| Benzyldimethyl [2-[2-(p-1,1,3,3-tetramethyl-butylphenoxy)ethoxy]ethyl]ammonium chloride (benzethonium chloride, U.S.P.) | 0.2 |
| N—dodecyl-2,2,2-trifluoroethylamine | 8.0 |
| Myristic acid | 2.0 |
| Stearic acid | 4.0 |
| Triethanolamine | 2.0 |
| Glyceryl monosterate | 3.0 |
| Polyoxyethylene (20) sorbitan mono-oleate | 3.0 |
| Polyoxyethylene (20) sorbitan monolaurate | 3.0 |
| Polyvinylpyrrolidone | 1.0 |
| Polyethylene glycol (average molecular weight, 600) | 1.4 |
| Deionized water | 72.4 |
| | 100.0 |

The procedure is repeated using as the active ingredient, in place of N-dodecyl-2,2,2-trifluoroethylamine, a similar percentage of any of the compounds prepared in accordance with Examples 3, 4 and 5.

Other similar formulations are prepared by repeating the procedure using, in place of N-dodecyl-2,2,2-trifluoroethylamine, an identical amount of one of the following compounds: N-alkyl pyridines such as N-nonyl, N-tridecyl, N-heptadecyl, and N-nonadecyl pyridine; 2-alkyl /pyridines such as 2-nonyl, 2-tridecyl, 2-heptadecyl, and 2-nonadecyl pyridines; N-alkyl morpholines such as N-decyl, N-dodecyl, N-tetradecyl, N-hexadecyl, and N-octadecyl morpholines, and alkyl-substituted imidazoles such as N-dodecylimidazole

EXAMPLE 8

Capsule Formulation

| | |
|---|---|
| N—dodecyl-2,2,2-trifluoroethylamine | 25 gm. |
| Stearic Acid (U.S.P. triple pressure) | 125 gm. |
| Pluronic F-68 | 7.5 gm. |
| Corn Starch | 125 gm. |

The stearic acid and pluronic are united in a vessel and melted using a water bach at 60°–65° C. The heating is discontinued and the N-dodecyl-2,2,2-trifluoroethylamine is dispersed into the mixture and the corn starch is added with stirring which is continued until the mixture cools to ambient temperature. The mixture is reduced to granules by screening and placed in a number 0 hard gelatin containing 282.5 mg. of total solids and 25 mg. of N-dodecyl-2,2,2-trifluoroethylamine per capsule.

This procedure is repeated using as the active ingredient any of the compounds prepared in accordance with Examples 3, 4, and 5, with resultant production of pharmaceutical formulations of the present invention.

Other formulations are prepared by repeating the procedure using the same amount of one of the following heterocyclic compounds: N-alkyl pyridines such as N-nonyl, N-tridecyl, N-heptadecyl, and N-nonadecyl pyridine; 2-alkyl pyridines such as 2-nonyl, 2-tridecyl, 2-heptadecyl, and 2-nonadecyl pyridines; N-alkyl morpholines such as N-decyl, N-dodecyl, N-tetradecyl, N-hexadecyl, and N-octadecyl morpholines, and alkyl-substituted imidazoles such as N-dodecylimidazole.

EXAMPLE 9

Carbobenzoxy-gly-pheamide of adriamycin

A solution of 35 mg [0.0609 mM] adriamycin hydrochloride (containing 175 mg lactose), 33.8 mg [0.0609 mM] carbobenzoxy-gly-phe hydroxy succinimic ester, and 16.8 μl triethylamine [0.12 mM] in 5 ml of dimethylformamide is prepared and stirred at room temperature (25° C.) for 24 hours. The solvent is evaporated in vacuo leaving a residual material containing the product which is dissolved in chloroform/methanol in a ratio of 99:1 by volume. The undissolved solid is removed by filtration and discarded. The filtrate containing the desired product is evaporated to dryness in vacuo and the residue containing the desired product is chromatographed on silica gel using chloroform/methanol (9:1) as the developing solvent. The principal product isolated is 40 mg of the title material NMR 200 MH$_3$.

EXAMPLE 10

N-Carbobenzoxy-glycyl-N,N-bis(2-chloroethyl)-L-phenylalanineamide

To 1.347 g. Bis-(2-chloroethyl)amine hydrochloride is added 100 ml 25% aqueous sodium hydroxide solution. The liberated amine is extracted into 100 ml methylene chloride, dried with potassium carbonate, filtered and evaporated to remove the methylene chloride solvent leaving 457 mg of the free amine. The residue is then dissolved in 15 ml tetrahydrofuran and is than added dropwise to 1.176 g N-carbobenzoxy-glycyl-L-phenylalanine dicyclohexyl carbodiamide in 50 ml tetrahydrofuran. The mixture is stirred at 0° under nitrogen for approximately 5 hours. It is then filtered and the filtrate evaporated to dryness leaving a residue which is dissolved in ethylacetate, washed with pH 2 aqueous phosphoric acid, aqueous potassium acid phosphate and salt solution. The ethyl acetate layer is then filtered and evaporated to dryness leaving as a residue 1.483 g of the desired product. TLC of 83 mg using 1:1 chloroform-ethylacetate yields 23 mg of substantially pure product. R$_f$=0.3.

EXAMPLE 11

N-(t-Butyloxycarbonyl)glycyl-N,N-di-(2-chloroethyl)-L-phenylalanineamide

N-(t-Butyloxycarbonyl)glycyl-L-phenylalanine is prepared by treating 2.22 g. glycyl-L-phenylalanine with 2.32 grams of butyloxycarbonyl anhydride and 1.39 ml dry ethylamine in methylene chloride for 3 hours at room temperature. The product is extracted into aqueous potassium acid phosphate solution and then back in the methylene chloride after acidification. Evaporation affords butyloxycarbonylglycyl-L-phenylalanineamide as a glass.

Mixture of 1.34 g nitrogen mustard free base, 3.04 g BOC-Gly-L-Phe and 2.01 grams of DCC (dicyclohexyldiamide) in tetrahydrofuran is stirred for 5 hours at room temperature 25° C., filtered, evaporated and taken up in ethyl acetate. The ethyl acetate layer is washed with water, aqueous phosphoric acid, aqueous potassium acid phosphate and salt solution, it is then dried with potassium carbonate, filtered and the solvent evaporated to a residue containing the product. The residue is then chromatographed on 80 g silica gel with 9:1 chloroform:methanol, Rf Ca. 0.5 yielding product in substantially pure form.

EXAMPLE 12

N-Carbobenzoxyglycyl-N-[2-(perfluorooctyl)ethyl]-L-phenylalanineamide

Part 1: Preparation of 2-(perfluoro-n-octyl)ethyl iodide.

19.5 g Perfluoro-n-octyl)ethyl iodide is placed in a flask equipped with gas inlet and water-cooled condensor topped with a dry ice condenser. Ethylene gas is admitted, 0.19 g benzoyl peroxide is added, and the mixture heated 5 hrs at 85° C. under ethylene. The product is obtained as a white powder, m.p. 54°-55.5° C. NMR: 2.3-2.9 m, 3.1-3.5 m MS: 574.

Part 2: Preparation of 2-(perfluoro-n-octyl)ethylamine.

The compound from Part 1 is placed into a bomb with 15 ml n-butenol and 1.33 g ammonia, and is heated to 80° C. for 3.5 hrs, cooled and vented. Then 10% aqueous sodium hydroxide is added and the mixture extracted with ether. Combined ether extracts of the amine are washed with brine, dried with potassium carbonate, filtered and treated with anhydrous hydrogenchloride. The solvents are evaporated under reduced pressure and the residue containing the product is washed with hexane affording the product as the hydrochloride in the form of a white powder. NMR (17.HCl, CD$_3$OD): 2.68 t of t, J=18, 7 Hz (C$\underline{H}_2$CF$_2$); 3.36 t, J=7 Hz (C$\underline{H}_2$NH$_3^{30}$).

Part 3: N-carbobenzoxyglycyl-N-[2-(perfluorooctyl)ethyl]-L-phenylalanineamide.

The hydrochloride obtained according to the previous example is converted to the free base by stirring with 20 ml methylene chloride, 10 ml 50% sodium hydroxide and 5 ml water for approximately 30 minutes. The aqueous layer is saturated with potassium carbonate. The organic layer containing the amine is decanted, dried with potassium carbonate, filtered and added at −10° C. to a stirred solution of 0.84 g carbobenzoxyglycylphenylalanine, 0.21 ml ethylamine and 0.140 ml ethyl chloroformate in methyl chloride. The reaction mixture is stirred under nitrogen for 3 hrs at −10° and 28 hrs at room temperature, approximately 25° C. The solvent is evaporated and replaced with ethylacetate. The ethylacetate solution of product is washed with aqueous phosphoric acid, water, aqueous potassium acid phosphate and salt solution, dried with magnesium sulfate, filtered and evaporated leaving a residue comprising substantially pure product.

What is claimed is:

1. A novel lysosomotropic detergent having a pK of from 3.5 to 8 of the formula:

wherein:

R$_1$ is C$_{8-30}$ alkyl;

2. A compound according to claim 1 wherein the compound is N-dodecyl-2,2,2-trifluoroethylamine.

3. A compound according to claim 1 wherein the compound is N-dodecyl-2,2-difluoroethylamine.

* * * * *

UNITED STATES PATENT AND TRADEMARK OFFICE
CERTIFICATE OF CORRECTION

PATENT NO. : 4,719,312
DATED : Jan. 12, 1988
INVENTOR(S) : RAYMOND A. FIRESTONE

It is certified that error appears in the above—identified patent and that said Letters Patent is hereby corrected as shown below:

On the Title Page:

Title Should Read:

"LYSOSOMOTROPIC DETERGENT THERAPEUTIC AGENTS"

not "LYSOSOMETROPIC DETERGENT THERAPEUTIC AGENTS"

Signed and Sealed this

Twelfth Day of July, 1988

Attest:

DONALD J. QUIGG

Attesting Officer

Commissioner of Patents and Trademarks